United States Patent [19]

Pietruszkiewicz et al.

[11] Patent Number: 4,731,472

[45] Date of Patent: Mar. 15, 1988

[54] (5,6-DICHLORO-3-OXO-9A-PROPYL-2,3,9,9A-TETRAHYDROFLUOREN-7-YL)AL-KANOIC ACIDS AND ALKANIMIDAMIDES

[75] Inventors: Adolph M. Pietruszkiewicz, North Wales; Otto W. Woltersdorf, Jr., Chalfont; Edward J. Cragoe, Jr., Lansdale, all of Pa.

[73] Assignee: Merck & Co., Inc., Rahway, N.J.

[21] Appl. No.: 835,598

[22] Filed: Mar. 3, 1986

[51] Int. Cl.$^4$ ............................................. C07C 59/86
[52] U.S. Cl. ...................................... 562/461; 560/51
[58] Field of Search ...................... 562/461; 560/51; 514/569, 545

[56] References Cited

U.S. PATENT DOCUMENTS

| | | | |
|---|---|---|---|
| 4,316,043 | 2/1982 | Cragoe et al. | 560/53 |
| 4,317,912 | 3/1982 | Cragoe et al. | 562/461 |
| 4,337,354 | 6/1982 | Cragoe et al. | 562/461 |
| 4,356,313 | 10/1982 | Cragoe et al. | 560/53 |
| 4,356,314 | 10/1982 | Cragoe et al. | 560/53 |

OTHER PUBLICATIONS

"Agents for the Treatment of Brain Injury", 1. (Aryloxy) Alkanoic Acids, Cragoe et al., J. Med. Chem., (1982), 25, 567–79.

*Primary Examiner*—Paul J. Killos
*Attorney, Agent, or Firm*—Charles M. Caruso; Hesna J. Pfeiffer

[57] ABSTRACT

The invention relates to novel [(5,6-dichloro-3-oxo-9a-propyl-2,3,9,9a-tetrahydrofluoren-7-yl)]alkanoic acids and alkanimidamides, their derivatives and their salts. The compounds are useful for the treatment and prevention of injury to the brain and of edema due to head trauma, stroke (particularly ischemic), arrested breathing, cardiac arrest, Reye's syndrome, cerebral thrombosis, cerebral embolism, cerebral hemorrhage, cerebral tumors, encephalomyelitis, spinal cord injury, hydrocephalus, post-operative brain injury trauma, edema due to cerebral infections, various brain concussions and elevated intracranial pressure.

10 Claims, No Drawings

(5,6-DICHLORO-3-OXO-9A-PROPYL-2,3,9,9A-TETRAHYDROFLUOREN-7-YL)ALKANOIC ACIDS AND ALKANIMIDAMIDES

BACKGROUND OF THE INVENTION

Trauma to the brain or spinal cord caused by physical forces acting on the skull or spinal column, by ischemic stroke, arrested breathing, cardiac arrest, Reye's syndrome, cerebral thrombosis, cerebral embolism, cerebral hemorrhage, encephalomyelitis, hydrocephalus, post-operative brain injury, cerebral infections, various concussions and elevated intracranial pressure results in edema and swelling of the affected tissues. This is followed by ischemia, hypoxia, necrosis, temporary or permanent brain and/or spinal cord injury and may result in death. The tissue mainly affected are classified as grey matter, more specifically astroglial cells. The specific therapy currently used for the treatment of the medical problems described include various kinds of diuretics (particularly osmotic diuretics), steroids (such as, 6-α-methylprednisolone succinate) and barbiturates. The usefulness of these agents is questionable and they are associated with a variety of untoward complications and side effects. Thus, the compounds of this invention comprise a novel and specific treatment of medical problems where no specific therapy is available.

A recent publication entitled "Agents for the Treatment of Brain Injury" 1. Aryloxy)alkanoic Acids, Cragoe et al, J. Med. Chem., (1982) 25, 567-79, reports on recent experimental testing of agents for treatment of brain injury and reviews the current status of treatment of brain injury. Additionally, U.S. Pat. Nos. 4,316,043, 4,317,922, 4,337,354, 4,356,313 and 4,356,314 disclose certain alkanoic and cycloalkanoic acids for the treatment of grey matter edema.

The compounds of the invention have the added advantage of being devoid of the pharmacodynamic, toxic or various side effects characteristic of the diuretics, steroids and barbiturates.

DESCRIPTION OF THE INVENTION

The compounds of the instant invention are best characterized by reference to the following structural Formula (I):

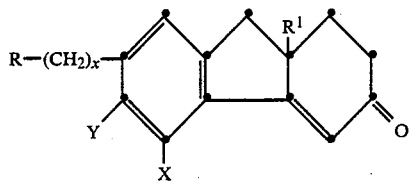

(I)

wherein:
R is —COOH,

$R^1$ is lower alkyl, branched or unbranched, containing from 1 to 5 carbon atoms such as methyl, ethyl, n-propyl, isopropyl and the like, aryl such as phenyl, halo substituted aryl such as p-fluorophenyl, o-fluorophenyl, p-chlorophenyl and the like, aralkyl such as benzyl, cycloalkyl containing from 3 to 6 nuclear carbon atoms such as cyclopropyl, cyclobutyl, cyclopentyl and the like, or cycloalkyl-lower alkyl containing from 4 to 7 total carbon atoms such as cyclopentylmethyl and the like;

$R^2$ is $NH_2$, $NHR^4$ or $NR^4R^5$;

$R^3$ is NH or $NR^4$;

$R^4$, $R^5$ are each independently lower alkyl, branched or unbranched, containing from 1 to 5 carbon atoms, or amino, provided that $R^4$ and $R^5$ are not both amino;

wherein $R^2$ and $R^3$ may be joined together via $R^4$ to form a heterocyclic ring of 5 or 6 atoms containing 2 nitrogen atoms and 3 or 4 carbon atoms, such as:

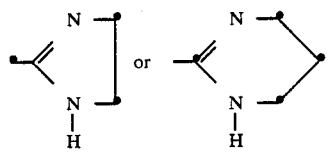

or wherein $R^4$ and $R^5$ may be joined together to form a 5- or 6-membered ring containing one nitrogen atom and 4 or 5 carbon atoms, such as:

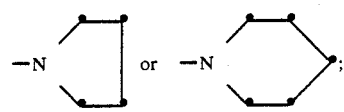

X and Y are halo or lower alkyl, such as methyl; and x is 1 to 4.

Since the 9a-carbon atom in the molecule is asymmetric, the compounds of the invention are racemic. However, these compounds or their precursors can be resolved so that the pure enantiomers can be prepared, thus the invention includes the pure enantiomers. This is an important point since some of the racemates consist of one enantiomer which is much more active than the other one. Furthermore, the less active enantiomer generally possesses the same intrinsic toxicity as the more active enantiomer. In addition, it can be demonstrated that the less active enantiomer depresses the inhibitory action of the active enantiomer at the tissue level. Thus, for three reasons it is advantageous to use the pure, more active enantiomer rather than the racemate.

Since the ethanimidamide products of the invention are basic, the invention also includes the obvious pharmaceutically acceptable acid addition salts such as the hydrochloride, hydrobromide, sulfate, isethionate, acetate, methanesulfonate, maleate, succinate and the like salts.

Likewise, since the alkanoic acid products of the invention are acidic, the invention also includes the obvious pharmaceutically acceptable salts such as the sodium, potassium, ammonium, trimethylammonium, piperazinium, 1-methylpiperazinium, guanidinium, bis-(2-hydroxyethyl)ammonium, N-methylglucosammonium and the like salts.

It is also to be noted that the compounds of Formula I, as well as their salts, often form solvates with the solvents in which they are prepared or from which they are recrystallized. These solvates may be used per se or they may be desolvated by heating (e.g. at 70° C.) in vacuo.

Although the invention primarily involves novel (5,6-dichloro-3-oxo-9a-propyl-2,3,9,9a-tetrahydrofluoren-7-yl)alkanoic acids and alkanimidamides, and their salts, it also includes their derivatives, such as oximes, hydrazones and the like. Additionally, this invention includes pharmaceutical compositions in unit dosage form containing a pharmaceutical carrier and an effective amount of a compound of Formula I, its R or S enantiomer, or the pharmaceutically acceptable salts thereof, for treating brain injury. The method of treating a person with brain injury by administering said compounds or said pharmaceutical compositions is also a part of this invention.

PREFERRED EMBODIMENT OF THE INVENTION

The preferred embodiments of the instant invention are realized in structural Formula II

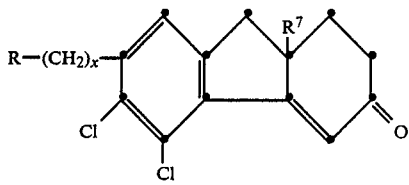

(II)

wherein:
R is as defined above;
$R^7$ is lower alkyl, branched or unbranched, containing from 1 to 5 carbon atoms; and
x is 1 or 2.

Also included are the enantiomers of each racemate.

A preferred compound is (5,6-dichloro-2,3,9,-9a,-tetrahydro-3-oxo-9a-propyl-1H-fluoren-7-yl)acetic acid.

Also preferred is 3-(5,6-dichloro-2,3,9,9a-tetrahydro-3-oxo-9a-propyl-1H-fluoren-7-yl)propionic acid.

Also preferred is (5,6,-dichloro-2,3,9,9a-tetrahydro-3-oxo-9a-propyl-1H-fluoren-7-yl)ethanimidamide hydrochloride.

Also preferred is (+)(5,6-dichloro-2,3,9,9a-tetrahydro-3-oxo-9a-propyl-1H-fluoren-5-yl)acetic acid.

Especially preferred are the pure enantiomers since, in most instances, one enantiomer is more active biologically then its antipode.

Included within the scope of this invention are the pharmaceutically acceptable salts of (5,6-dichloro-3-oxo-9a-propyl-2,3,9,9a-tetrahydrofluoren-7-yl)alkanoic acids and alkanimidamides since a major medical use of these compounds is solutions of their soluble salts which can be administered parenterally.

Thus, the acid addition salts can be prepared by the reaction of the (5,6-dichloro-3-oxo-9a-propyl-2,3,9,9a-tetrahydrofluoren-7-yl)alkanoic acids of this invention with an appropriate alkali metal hydroxide, carbonate or bicarbonate such as sodium hydroxide, potassium hydroxide, sodium carbonate, sodium bicarbonate and the like or an organic base, such as ammonium hydroxide, piperazine, 1-methylpiperazine, guanidine, bis-(2-hydroxyethyl)amine, N-methylglucosamine and the like salts of the alkanimidamides of this invention may be prepared by reaction with an appropriate pharmaceutically acceptable mineral acid or organic carboxylic acid, such as hydrochloric acid, sulfuric acid, hydrobromic acid, isethionic acid, methanesulfonic acid, maleic acid, succinic acid, acetic acid and the like. The salts selected are derived from among the non-toxic, pharmaceutically acceptable acids.

The synthesis of the compounds of this invention in which R=COOH and x=1 (Ia) is accomplished by the following seven-step series of reactions.

Treatment of the indanone of Formula III with sodium hydride in a mixture of solvents like dimethylformamide and toluene followed by reaction with 1,3-dichloro-2-butene in toluene at a temperature of about 50°-55° C. for a period of about 3 hours gave the diketone of Formula IV.

Treatment of compound of Formula IV with molten pyridine hydrochloride at 175°-185° C. for a period of about 1 to 2 hours gave the phenol of Formula V.

The reaction of the phenol of Formula V with trifluoromethane sulfonyl chloride in dimethylformamide containing potassium carbonate gave the trifluoromethylsulfonyl ester of Formula VI.

The reaction of diethyl malonate with sodium hydride in a mixture of dimethylformamide and toluene followed by treatment with the compound of Formula VI at 5° to 7° C. for about a total time of 30 to 60 minutes and then at ambient temperature produced the cmpound of Formula VII upon acidification in water.

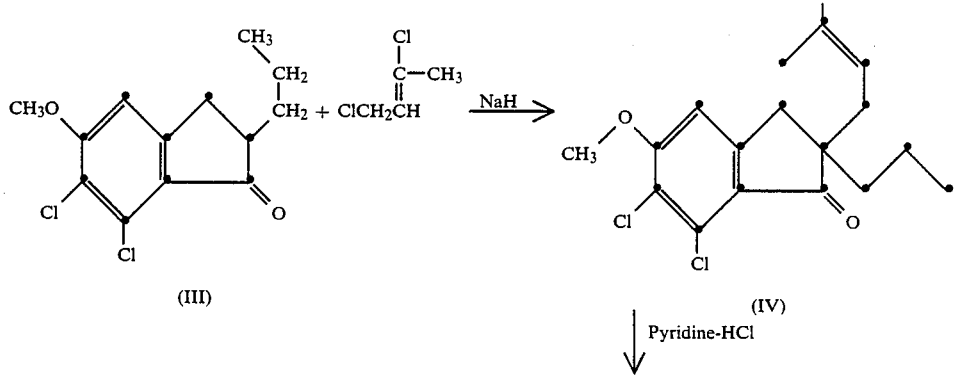

-continued

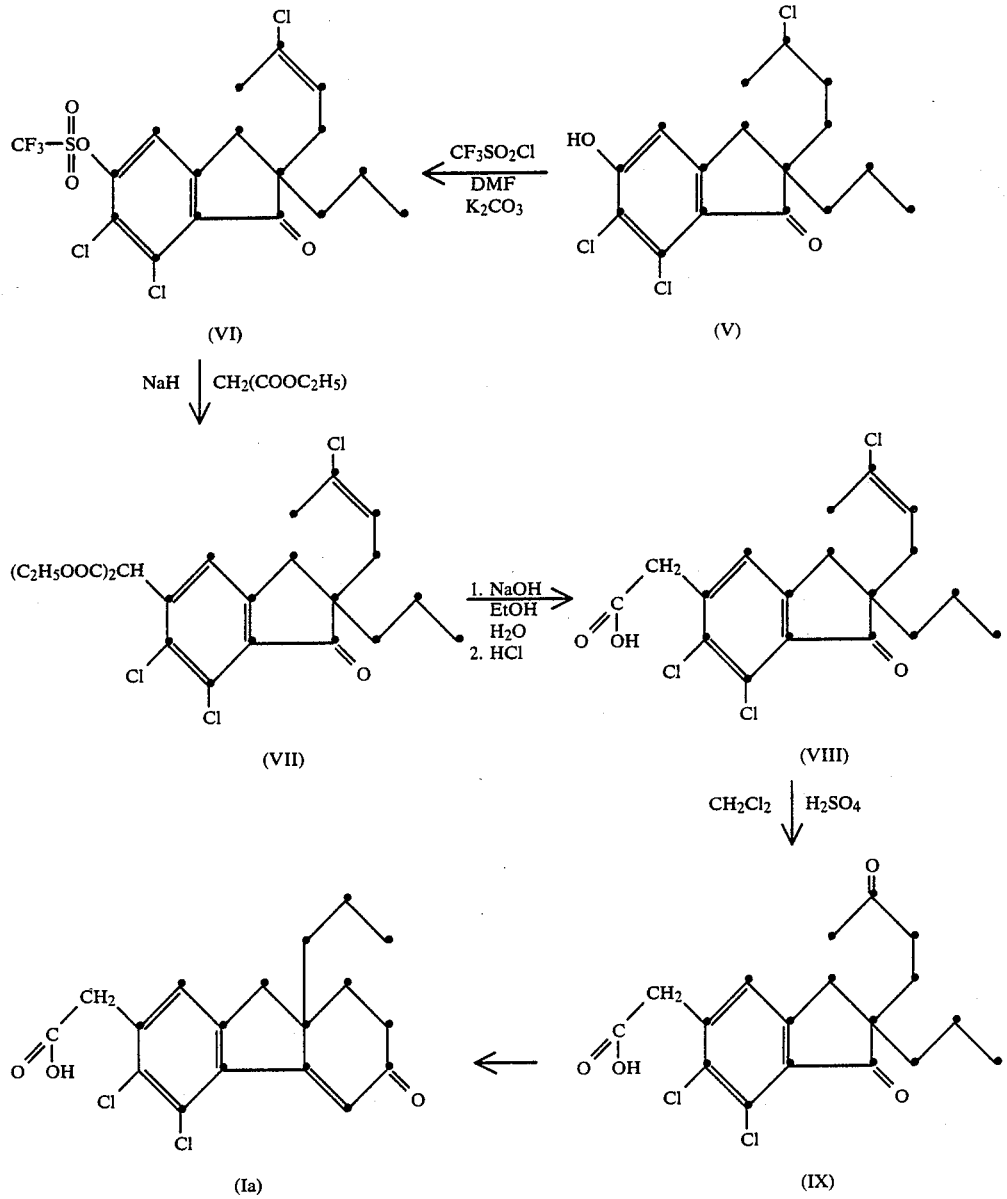

Saponification and decarboxylation of the compound of Formula VII to produce the compound of Formula VIII was accomplished by refluxing in an aqueous ethanolic solution of sodium hydroxide for about ¾ to 2 hours followed by acidification with hydrochloric acid.

Conversion of the compound of Formula VIII to the diketone of Formula IX was accomplished by treatment with concentrated sulfuric acid in methylene chloride for a period of 30 minutes to 2 hours at 0° to 5° C.

Cyclization of the compound of Formula IX to the desired product of Formula I was accomplished by treatment with aqueous sodium hydroxide at ambient temperature for a period of 50 to 100 hours followed by acidification with hydrochloric acid.

The compound of the invention where R=COOH and X=2 (Ib) and prepared by the following five-step series of reactions.

Treatment of the compound of Formula VII with sodium hydride in a mixture of diemthylformamide and toluene followed by reaction with methyl bromoacetate at 60°-70° C. for 4 to 6 hours followed by by the additional of aqueous acid produced the compound of Formula X.

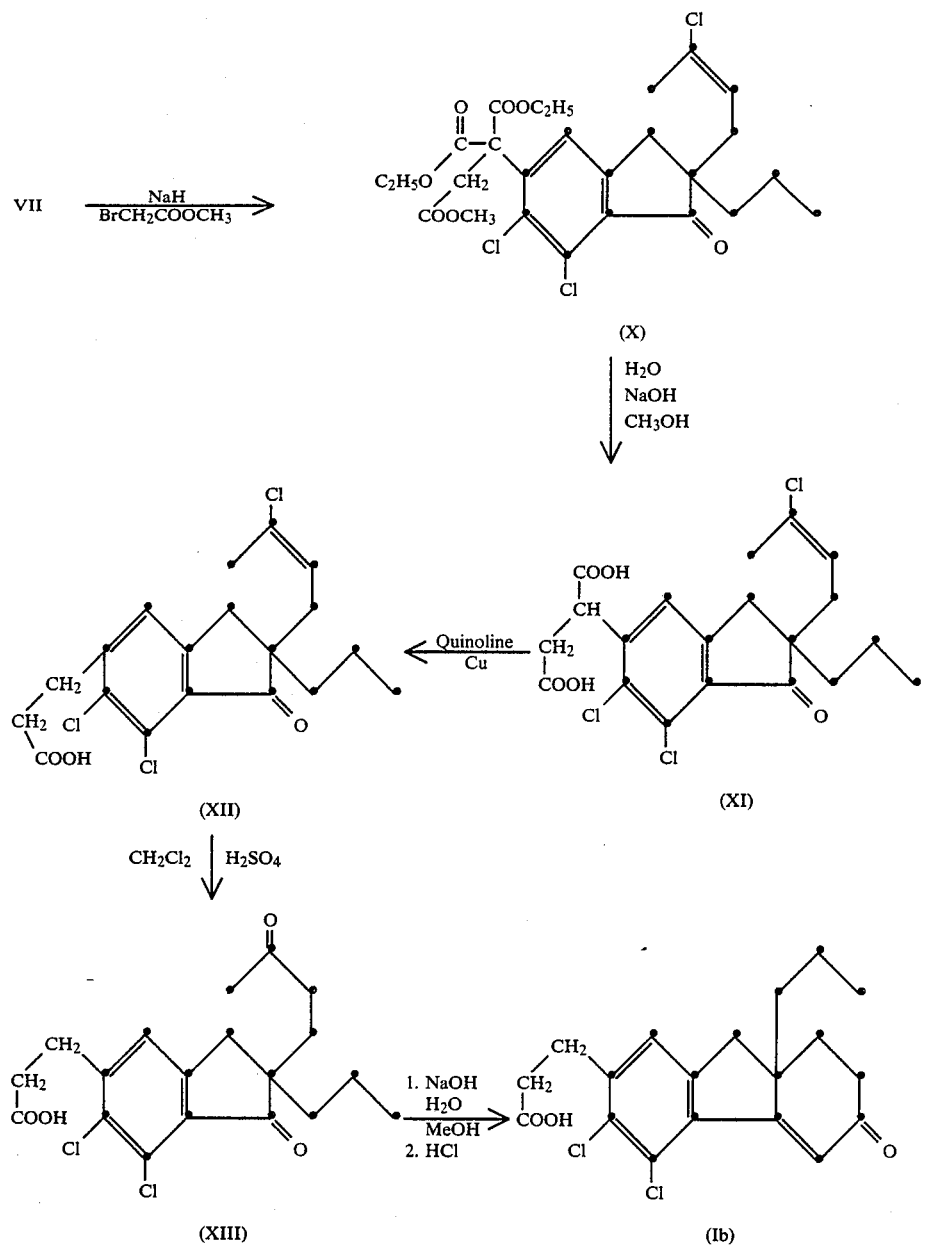

Saponification and decarboxylation of the compound of Formula X to the compound of Formula XI occurred by heating in a mixture of methanol, water and sodium hydroxide for a period of 2 to 3 hours followed by acidification.

Heating the compound of Formula XI with quinoline and copper powder at 130°-135° C. for 20 to 40 minutes produced the compound of Formula XII upon treatment with aqueous acid.

The treatment of the compound of Formula XII with concentrated sulfuric acid and methylene chloride at 0°-5° C. for 20 minutes to 1 hour produced the diketone of Formula XIII upon addition to water.

Cyclization of the diketone of Formula XIII to the desired product of Formula Ib occurred upon treatment with an aqueous methanolic solution of sodium hydroxide at ambient temperature for 50 to 100 hours followed by acidification.

It is to be recognized that these compounds of Formula I possess an asymmetric carbon atom at position 9a and, therefore, consist of racemates composed of two enantiomers. The resolution of the two enantiomers may be accomplished by forming a salt of the racemic mixture with an optically active base such as (+) or (−) amphetamine, (−) cinchonidine, dehydroabietylamine, (+) or (−)-α-methylbenzylamine, (+) or (−)-α-(1-naphthyl)ethylamine, (+) cinchonine, brucine. or strychnine and, the like in a suitable solvent such as methanol, ethanol, 2-propanol, benzene, acetonitrile, nitromethane, acetone and the like. There is formed in the solution two diastereomeric salts one of which is usually less soluble in the solvent than the other. Repetitive recrystallization of the crystalline salt generally affords a pure diastereomeric salt from which is obtained the desired pure enantiomer. The optically pure enantiomer is obtained by acidification of the salt with a mineral acid, isolation by filtration and recrystallization of the optically pure antipode.

The other optically pure antipode may generally be obtained by using a different base to form the diastereomeric salt. It is of advantage to isolate the partially resolved acid from the filtrates of the purification of the first diastereomeric salt and to further purify this substance through the use of another optically active base. It is especially advantageous to use an optically active base for the isolation of the second enantiomer which is the antipode of the base used for the isolation of the first enantiomer. For example, if (+)-α-methylbenzylamine was used first, then (−)-α-methylbenzylamine is used for the isolation of the second (remaining) enantiomer.

Since the products of Formulas Ia and Ib the invention are acidic, the invention also includes the obivous pharmaceutically acceptable salts such as the sodium, potassium, ammonium, trimethylammonium, piperazinium, 1-methylpiperazinium, guanidinium, bis-(2-hydroxethyl)ammonium, N-methylglucosammonium and the like salts.

The compounds of the invention where $$R = -\overset{NH}{\underset{}{\overset{\|}{C}}} - NH_2$$

are prepared as follows (x=1 or 2):

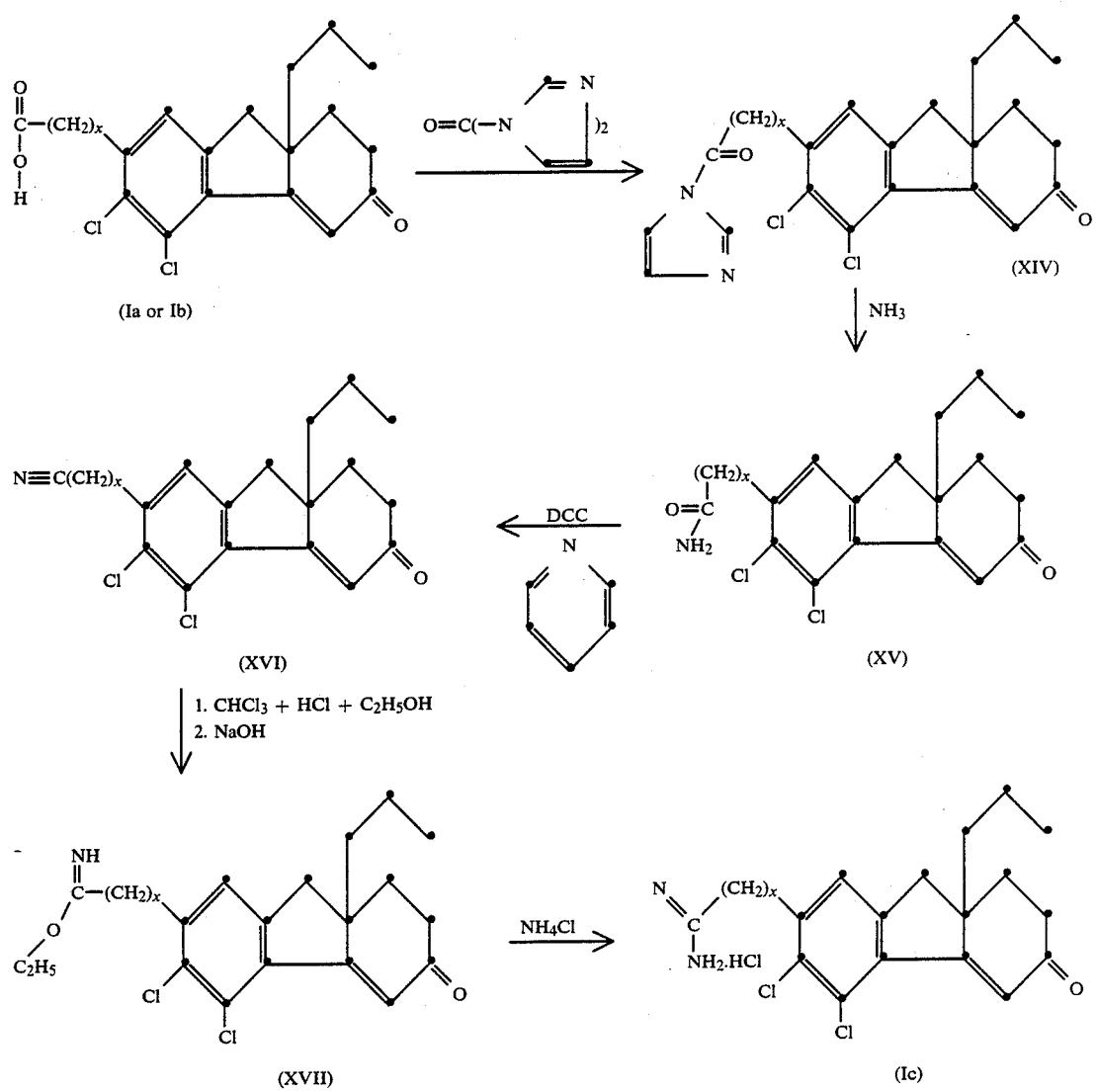

The reaction of a compound of the invention of Formula Ia (i.e., Ia or Ib) with 1,1'-carbonyldiimidazole in a solvent such as tetrahydrofuran produces a acylimidazole of Formula XIV which is generally not isolated but treated in situ with ammonia to give the amide of Formula XV.

The reaction of an amide of Formula XV with dicyclohexylcarbodiimide (DCC) in pyridine at ambient temperature for 3 to 10 hours followed by removal of the dicyclohexylurea and excess pyridine gives a nitrile of Formula XVI.

Dissolving the nitrile of Formula XVI in chloroform containing about 1.1 mole equivalent of ethanol and saturating the solution with hydrogen chloride at 0° to 5° C. and allowing to stand for 10–20 hours produces the hydrochloride salt of the imino ester of Formula XVII. Basification of this hydrochloride salt with sodium hydroxide gives the free imino ester which upon treatment with ammonium chloride in aqueous ethanol produced the desired alkanimidamide hydrochloride of Formula Ic.

It is to be noted that if the Ic used as a starting material for this sequence of reactions is racemic, the product of Formula Id is racemic. However, if a pure enantiomer of Formula Ic is used as the starting material, the product of Formula Id is a pure enantiomer.

Since the compounds of Formula Id are hydrochloride salts of a base, other salts, particularly the pharmaceutically acceptable ones, such as the hydrobromide, the sulfate, the methanesulfonate, the isethionate, the succinate, the maleate and the like constitute a part of this invention. These salts can be made by substituting the corresponding ammonium salt in place of ammonium chloride (which produces the hydrochloride salt). Alternatively, the salts of Formula Id may be converted to the free base with a base much as sodium hydroxide followed by treatment with the desired acid to obtain the desired salt.

Those compounds possessing an asymmetric carbon atom at the 9a-position of the molecule consist of a racemate composed of two enantiomers.

The preferred synthesis of the pure enantiomers of this invention is to initiate the synthesis with the enantiomerically pure phenol of formula III. Alternatively, the resolution of the racemic compounds of formula I may be accomplished by forming a salt of the racemic mixture with an optically active acid such as (+) and (−)-malic acid, (+) and (−)-dibenzoyltartaric acid, (+) and (−)-α-methoxy-α-(trifluoromethyl)phenylacetic acid, (+) and (−)-tartaric acid, d- and 1-10-camphorsulfonic acid, d- and 1-α-bromo-camphor-π- sulfonic acid and the like in a suitable solvent such as methanol, ethanol, 2-propanol, benzene, acetonitrile, nitromethane, acetone and the like. There is formed in the solution, two diastereomeric salts, one of which is usually less soluble in the solvent than the other. Repetitive recrystallization fo the crystalline salt generally affords a pure diastereomeric salt form which is obtained the desired pure enantiomer. The optically pure enantiomer of the compound of Formula I is obtained by reaction of the salt with a base, isolation by filtration and recrystallization of the optically pure antipode.

The other optically pure antipode may generally be obtained by using a different acid to form the diastereomeric salt. It is of advantage to isolate the partially resolved base from the filtrates of the purification resolved base from the filtrates of the purification of the first diastereomeric salt and to further purify this substance through the use of another optically active acid. It is especially advantageous to use an optically active acid for the isolation of the second enantiomer which is the antipode of the acid used for the isolation of the first enantiomer. For example, if (−)-malic acid was used first, then (+)-malic acid is used for the isolation of the second (remaining) enantiomer.

The acid addition salts are prepared by reacting the bases of Formula I with an appropriate acid, for example, aqueous mineral acids, carboxylic acids or other organic acids, such as hydrochloric acid, sulfuric acid, isethionic acid, methanesulfonic acid, acetic acid and the like. If the compound is already in the form of a salt and a different salt is desired the initial salt may be reacted with a base such as sodium hydroxide to generate the free base which in turn may be reacted with another acid to form a new salt.

The reaction may be conducted in water but it is preferred to conduct the reaction in an organic solvent, such as ether, ethanol, N,N-dimethylformamide and the like.

The preferred salts are the pharmaceutically acceptable salts such as the hydrochloride salts and the like.

Inasmuch as there are a variety of symptoms and severity associated with grey matter edema, particularly when it is caused by head trauma, stroke, cerebral hemorrhage or embolism, post-operative brain surgery trauma, spinal cord injury, cerebral infections, various brain concussions and elevated intracranial pressure, the precise treatment is left to the practioner. Generally, candidates for treatment will be indicated by the results of the patient's initial general neurological status, findings on specific clinical brain stem functions and findings on computerized axial tomography (CAT), nuclear magnetic resonance (NMR) or positron emission tomography (PET) scans of the brain. The sum of the neurological evaluation is presented in the Glascow Coma Score or similar scoring system. Such a scoring system is often valuable in selecting the patients who are candidates for therapy of this kind.

The compounds of this invention can be administered by a variety of established methods, including intravenously, intramuscularly, subcutaneously, or orally. The parenteral route, particularly the intravenous route of administration, is preferred, especially for the very ill and comatose patient. Another advantage of the intravenous route of administration is the speed with which therapeutic brain levels of the drug are achieved. It is of paramount importance in brain injury of the type described to initiate therapy as rapidly as possible and to maintain it through the critical time periods. For this purpose, the intravenous administration of drugs of the type of Formula I in the form of their salts is superior.

A recommended dosage range for treatment is expected to be from 0.05 mg/kg to 50 mg/kg of body weight as a single dose, preferably from 0.5 mg/kg to 20 mg/kg. An alternative to the single dose schedule is to administer a primary loading dose followed by a sustaining dose of half to equal the primary dose, every 4 to 24 hours. When this multiple dose schedule is used the dosage range may be higher than that of the single dose method. Another alternative is to administer an ascending dose sequence of an initial dose followed by a sustaining dose of 1½ to 2 times the initial dose every 4 to 24 hours. For example, 3 intravenous doses of 8, 12 and 16 mg/kg of body weight can be given at 6 hour intervals. If necessary, 4 additional doses of 16 mg/kg of body weight can be given at 12 hour intervals. Another effective dose regimen consists of a continuous intravenous infusion of from 0.05 mg/kg/hr to 3.0 mg/kg/hr. Of course, other dosing schedules and amounts are possible.

One aspect of this invention is the treatment of persons with grey matter edema by concomitant administration of a compound of Formula I or its salts, and an antiinflammatory steroid. These steroids are of some, albeit limited, use in control of white matter edema associated with ischemic stroke and head injury. Steroid therapy is given according to established practice as a supplement to the compound of Formula I as taught elsewhere herein. Similarly, a barbiturate may be administered as a supplement to treatment with a compound of Formula I.

The compounds of Formula I are utilized by formulating them in a pharmaceutical composition such as tablet, capsule or elixir for oral administration. Sterile solutions or suspensions can be used for parenteral administration. A compound or mixture of compounds of Formula I, or its physiologically acceptable salt, is compounded with a physiologically acceptable vehicle, carrier, excipient, binder, preservative, stabilizer, flavor, etc. in a dosage form as called for by accepted pharmaceutical practice.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection or infusion can be formulated according to conventional pharmaceutical practice by dissolving the active substance in a conventional vehicle such as water, saline or dextrose solution by forming a soluble salt in water using an appropriate acid, such as a pharmaceutically acceptable carboxylic acids or mineral acids. Alternatively, a suspension of the active substance in a naturally occurring vegetable oil like sesame oil, coconut oil, peanut oil, cottonseed oil, etc., or a synthetic fatty vehicle like ethyl oleate or the like may be formulated for injection or infusion. Buffer, preservatives, antioxidants and the like can be incorporated as required.

The basic premise for the development of agents for the treatment of brain injury of the types described is based on the studies in experimental head injury by R. S. Bourke et. al. (R. S. Bourke, M. A. Daze and H. K. Kimelberg, Monograph of the International Glial Cell symposium, Leige, Bel. Aug. 29–31, 1977 and references cited therein) and experimental stroke by J. H. Garcia et. al. (J. H. Garcia, H. Kalimo, Y. Kamijyo and B. F. Trump, Virchows Archiv. [Zellopath.], 25, 191 (1977).

These and other studies have shown that the primary site of traumatic brain injury is in the grey matter where the process follows a pattern of insult, edema, ischemia, hypoxia, neuronal death and necrosis followed, in many instances, by irreversible coma or death. The discovery of a drug that specifically prevents the edema would obviate the sequalae.

Experimental head injury has been shown to produce a pathophysiological response primarily involving swelling of astroglial as a secondary, inhibitable process. At the molecular level, the sequence appears to be: trauma, elevation of extracellular $K^+$ and/or release of neurotransmitters, edema, hypoxia and necrosis. Astroglial swelling results directly from a $K^+$-dependent, cation-coupled, chloride transport from the extracellular into the intracellular compartment with a concomitant movement of an osmotic equivalent of water. Thus, an agent that specifically blocks chloride transport in the astroglia is expected to block the edema caused by trauma and other insults to the brain. It is also important that such chloride transport inhibitors be free or relatively free of side effects, particularly those characteristics of many chloride transport inhibitors, such as diuretic properties. Compounds of the type illustrated by Formula I exhibit the desired effects on brain edema and are relatively free of renal effects.

That this approach is valid has been demonstrated by the correlation of the in vitro astroglial edema inhibiting effects of chloride transport inhibitors with their ability to reduce the mortality of animals receiving experimental in vivo head injury. As a final proof, one compound (ethacrynic acid) which exhibited activity both in vitro and in vivo assays was effective in reducing mortality in clinical cases of head injury. These studies are described in the Journal of Medicinal Chemistry, Volume 25, page 567 (1982), which is hereby incorporated by reference.

Three major biological assays can be used to demonstrate biological activity of the compounds. The (1) in vitro cat cerebrocortical tissue slice assay, (2) the in vitro primary rat astrocyte culture assay and (3) the in vivo cat head injury assay. The first assay, the in vitro cat cerebrocortical tissue slice assay has been described by Marshall, L. F.; Shapiro, H. M.; Smith, R. W. In "Seminars in Neurological Surgery: Neural Trauma"; Popp, A. J.; Bourke, R. S.; Nelson, L. R. ; Kimelberg, H, K,. Eds.; Raven Press: New York, 1979; p. 347, by Bourke, R. S.; Kimelberg, H, K.; Daze, M. A. in Brain Res. 1978, 154, 196, and by Bourke, R. S.; Kimelberg, H. K,; Nelson, L. R. in Brain Res. 1976, 105, 309. This method constitutes a rapid and accurate method of determining the intrinsic chloride inhibitory properties of the compounds of the invention in the target tissue.

The second assay method involves the in vitro primary rat astrocyte assay. The method has been described by Kimelberg, H. K.; Biddlecome, S.; Bourke, R. S. in Brain Res. 1979, 173, 111, by Kimelberg, H. K.; Bowman, c.; Biddlecome, S.; Bourke, R. S., in Brain Res. 1979, 177, 533, and by Kimelberg, H. K.; Hirata, H. in Soc. Neurosci. Abstr. 1981, 7, 698. This method is used to confirm the chloride transport inhibiting properties of the compounds in the pure target cells, the astrocytes.

The third assay method, the in vivo cat head injury assay has been described by Nelson, L. R.; Bourke, R. S.; Popp, A. J.; Cragoe, E. J. Jr.; Signorelli, A.; Foster, V. V. ; Creel, in Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H. K., Eds.; Raven Press: New York, 1979; p. 297.

This assay consists of a highly relevant brain injury in cats which is achieved by the delivery of rapid repetitive acceleration-deceleration impulses to the animal's head followed by exposure of the animals to a period of hypoxia. The experimental conditions of the assay can be adjusted so that the mortality of the control animals falls in the range of about 25 to 75%. Then, the effect of the administration of compounds of this invention in reducing the mortality over that of the control animals in concurrent experiments can be demonstrated.

Using the in vitro cat cerebrocortical tissue slice assay, described in Example 1, compounds of the present invention can be tested for activity. This test provides the principal in vitro evaluation and consists of a determination of concentration vs. response curve. The addition of $HCO_3^-$ to isotonic, $K^+$-rich saline-glucose incubation media is known to specifically stimulate the transport of $Cl^-$ coupled with $Na^+$ and an osmotic equivalent of water in incubating slices of mammalian cerebral cortex. Experiments have demonstrated that the tissue locus of swelling is an expanded astroglial compartment. Thus, the addition of $HCO_3^-$ to incubation media stimulates statistically significant and comparable increases in cerebrocortical tissue swelling and ion levels. After addition of drug to the incubation media, detailed drug concentration-response curves are then obtained. The data are expressed as percent $HCO_3^-$-stimulated swelling vs. drug concentration, from which the concentration of drug providing 50% inhibition of $HCO_3^-$-stimulated swelling ($I_{50}$ in molarity) is interpolated.

The following examples are included to illustrate the in vitro cerebrocortical tissue slice assay, the preparation of representative compounds of Formula I and representative dosage forms of these compounds. It is intended that the specification and examples be considered as exemplary only, with the true scope and spirit of the invention being indicated by the following claims. All temperatures in the examples are in Centigrade unless otherwise indicated.

EXAMPLE 1

In Vitro Cerebrocortical Tissue Slice Assay

Adult cats of 2–3 kg body weight are employed in tissue slice studies. Prior to sacrifice, the animals are anesthetized with ketamine hydrochloride (Ketaset), 10 mg/kg intramuscularly. Eight (three control, five experimental) pial surface cerebrocortical tissue slices (0.5-mm thick; approximately 150 mg initial fresh weight) are cut successively with a calibrated Stadie-Riggs fresh tissue microtome without moistening and weighed successively on a torsion balance. During the slice preparation all operations except weighing are confined to a humid chamber. Each slice is rapidly placed in an individual Warburg flask containing 2 ml of incubation medium at room temperature. The basic composition of the incubation media, in millimoles per liter, is as follows: glucose, 10; $CaCl_2$, 1.3; $MgSO_4$, 1.2; $KHSO_4$, 1.2; Hepes (N-2-hydroxyethylpiperazine-N'-2-ethanesulfonic acid, titrated with NaOH to pH 7.4), 20. Except when adding $HCO_2^-$, the osmolarity of the media is maintained isosmotic (approximately 285 mOsm/L) by reciprocal changes of $Na^+$ or $K^+$ to achieve a concentration of $K^+$ of 27 mM. The basic medium was saturated with oxygen by bubbling pure oxygen through the solution for 30 minutes before use. When added, $NaHCO_3$ or triethylammonium bicarbonate (TEAB) is initially present in the sidearm of each flask at an initial concentration of 50 mM in 0.5 ml of complete medium. Nonbicarbonate control slices are incubated at 37° C. in 2.5 ml of basic medium for 60 minutes. Bicarbonate control slices are similarly incubated for an initial 20 minutes at 37° C. in 2.0 ml of basic medium to which is added from the sidearm an additional 0.5 ml of incubation medium containing 50 mM $HCO_3^-$, which, after mixing, results in a $HCO_3^-$ concentration of 10 mM and a total volume of 2.5 ml. The incubation is continued for an additional 40 minutes. The various compounds to be tested are dissolved by forming the hydrochloride salts in water. When only the free bases are available, the hydrochloride salts are formed by treating the free base with a molar equivalent of hydrochloric acid and diluting to the appropriate concentrations. Just prior to incubation, all flasks containing $HCO_3^-$ are gassed for 5 minutes with 2.5% $CO_2$/97.5% $O_2$ instead of 100% $O_2$.

Following the 60-minute incubation period, tissue slices are separated from incubation medium by filtration, reweighed, and homogenized in 1N $HClO_4$ (10% w/v) for electrolyte analysis. The tissue content of ion is expressed in micromoles per gram initial preswelling fresh weight. Control slice swelling is expressed as microliters per gram initial preswelling fresh weight. The effectiveness of an inhibitor at a given concentration is measured by the amount of $HCO_3^-$-stimulated swelling that occurred in its presence, computed as a percent of the maximum possible. Tissue and media $Na^+$ and $K^+$ levels are determined by emission flame photometry with $Li^+$ internal standard; $Cl^-$ levels are determined by amperometric titration. Tissue viability during incubation is monitored by manometry.

EXAMPLE 2

(5,6-Dichloro-2,3,9,9a-tetrahydro-3-oxo-9a-propyl-1H-fluoren-7-yl)acetic acid Step A:

6,7-Dichloro-2-(3-chloro-2-butenyl)-2,3-dihydro-5-methoxy-2-propyl-1H-inden-1-one 6,7-Dichloro2,3-dihydro-5-methoxy-2-propyl-1H-indent-1-one (13.66 g, 0.05 mole) dissolved in toluene (80 ml) was added over 15 minutes with stirring under $N_2$ to a suspension of 56% sodium hydride (2.36 g, 0.055M) in dimethylformamide (65 ml) and toluene (15 ml) at 25°. The mixture was stirred without external heat for 1½ hours, at 50° C. for ½ hour and then cooled to 30° C. A solution of 1,3-dichloro-2-butene (7.81 g, 0.0625 mole) in toluene (10 ml) was added, and the mixture was heated at 50°–55° for 2 hours, poured into ice water, and extracted with diethyl ether. The organic extracts were washed with water, dried over $MgSO_4$, concentrated under vacuum and chromatographed on silica with elution with 1/1 hexane/methylene chloride to obtain 14.5 g of product as an oil which was a mixture of cis-trans isomers.

Step B:

6,7-Dichloro-2-(3-chloro-2-butenyl)-2,3-dihydro-5-hydroxy-2-propyl-1H-inden-1-one 6,7-Dichloro-2-(3-chloro-2-butenyl-2,3-dihydro-5-methoxy-2-propyl-1H-inden-1-one (40.3 g, 0.1114 moles) was added to stirring molten pyridine hydrochloride (350 g) and the mixture was heated for 1¼ hours under $N_2$ in an oil bath at an internal temperature of 175°–185° C. The molten mixture was poured over ice and extracted with a mixture of diethyl ether and tetrahydrofuran. The organic extracts were washed repeatedly with water, dried over $MgSO_4$ and concentrated under vacuum to obtain 36.8 g of product as a mixture of cis and trans isomers which after crystallization from isopropanol melted at 191°–3°.

| Calc for $C_{16}H_{17}Cl_3O_2$: | C, 55.27 | Found: | 55.63 |
|---|---|---|---|
| | H, 4.93 | | 4.99 |

Step C:

6,7-Dichloro-2-(3-chloro-2-butenyl)-2,3-dihydro-2-propyl-5-trifluoromethanesulfonyl-oxy-1H-inden-1-one 6,7-Dichloro-2-(3-chloro-2-butenyl)-2,3-dihydro-5-hydroxy-2-propyl-1H-inden-1-one (24.5 g, 0.0716 mole) was stirred for 1¼ hours at 25° C. in a mixture of potassium carbonate (29.7 g, 0.215 mole) in dimethylformamide (85 ml). The suspension was cooled to 10° C. and trifluoromethanesulfonyl chloride (14.6 g, 0.087 mole) was added. The mixture was stirred ½ hour at 10° C., 1½ hours at 25° C. and then poured over ice and extracted with diethyl ether. The organic extracts were washed with water, dried over MgSO₄ and concentrated under vacuum to obtain 33.7 g of the product as an oil.

Step D: Diethyl 2-[6,7-dichloro-2-(3-chloro-2-butenyl)-2,3-dihydro-1-oxo-2-propyl-1H-inden-5-yl]malonate Diethyl malonate (31.35 g, 0.196 mole) was added dropwise with stirring under N₂ at 10°–15° C. over 35 minutes to a suspension of 56% of sodium hydride in mineral oil (8.39 g, 0.196 mole) in dimethylformamide (135 ml) and toluene (35 ml). The mixture was stirred for 1.25 hours at 20°–25° C. after the addition of the malonate. The mixture as then cooled to 5° C. and 6,7-dichloro-2-(3-chloro-2-butenyl)-2,3-dihydro-2-propyl-5-trifluoromethanesulfonyloxy-1H-inden-1-one (33.7 g, 0.0702 mole) in toluene (40 ml) was added over 45 minutes at 5°–7° C. and then stirred 2½ hours at 20°–25° C., poured over ice and water and extracted with diethyl ether. The organic extracts were washed with dilute potassium carbonate, water, dried over MgSO₄ and concentrated under vacuum to obtain 59 g of product contaminated with mineral oil and diethyl malonate. Pure VII was obtained as an oil after elution chromatography on silica gel with methylene chloride/hexane as a 2/1 mixture.

Step E: [6,7-Dichloro-2-(3-chloro-2-butenyl)-2,3-dihydro-1-oxo-2-propyl-1H-inden-5-yl]acetic acid Crude diethyl 2-[6,7-dichloro-2-(3-chloro-2-butenyl)-2,3-dihydro-1-oxo-2-propyl-b 1H-inden-5yl]malonate (36.9 g, 0.075 mole) was refluxed with stirring in a mixture of ethanol (100 ml), water (100 ml) and sodium hydroxide (15 g) for 2 hours. The reaction mixture was cooled, diluted with water and extracted with hexane. The aqueous layer was acidified with hydrochloric acid and extracted with methylene chloride. The organic extracts were washed with water, dried over MgSO₄ and concentrated under vacuum to obtain 17 g of product which after recrystallization from a mixture of methyl cyclohexane and butyl chloride melted at 111°–114° C. and was shown by HPLC to be a 95% trans, 5% cis mixture.

| Calcd for C₁₈H₁₉Cl₃O₃: | C, 55.97 | Found: | 55.47 |
|---|---|---|---|
| | H, 4.91 | | 4.90 |

Step F: [6,7-Dichloro-2,3-dihydro-1-oxo-2-(3-oxobutyl)-2-propyl-1H-inden-5-yl]acetic acid

[6,7-Dichloro-2-(3-chloro-2-butenyl)-2,3-dihydro-1-oxo-2-propyl-1H-inden-5-yl]acetic acid (6 g, 0.0154 mole) dissolved in methylene chloride (65 ml) was added with rapid stirring to a mixture of H₂SO₄ (75 ml) and methylene chloride (35 ml) chilled in an ice bath. After stirring 1 hour at ice bath temperature the mixture was poured over ice and extracted with diethyl ether. The ether extracts were washed with water, dried over MgSO₄ and concentrated under vacuum. The residue was recrystallized from butyl chloride to obtain the product mp 137°–9°.

| Calcd for C₁₈H₂₀Cl₂O₄: | C, 58.23 | Found: | 58.36 |
|---|---|---|---|
| | H, 5.43 | | 5.61 |

Step G: (5,6-Dichloro-2,3,9,9a-tetrahydro-3-oxo-9a-propyl-1H-fluoren-7-yl)acetic acid

[6,7-Dichloro-2,3-dihydro-1-oxo-2-(3-oxo-butyl)-2-propyl-1H-inden-5-yl]acetic acid (3.0 g, 0.00808 mole) was dissolved in 25 ml 1N sodium hydroxide and 6 ml water, stirred at room temperature for 70 hours and then the reaction was diluted with water and acidified with hydrochloric acid. The product was extracted with methylene chloride, the organic extracts were washed with water, dried over MgSO₄, concentrated under vacuum and the residue recrystallized from acetonitrile to obtain the product, mp 206°–8°C.

| Calcd for C₁₈H₁₈Cl₂O₃: | C, 61.20 | Found: | 61.95 |
|---|---|---|---|
| | H, 5.14 | | 5.31 |
| | Cl, 20.07 | | 19.68 |
| HPLC, 100% & 99.1% | | | |

EXAMPLE 3

3-(5,6-Dichloro-2,3,9,9a-tetrahydro-3-oxo-9a-propyl-1H-fluoren-7-yl)propionic acid

Step A: Diethyl methoxycarbonylmethyl[6,7-dichloro-2-(3-chloro-2-butenyl)-2,3-dihydro-1-oxo-2-propyl-1H-inden-5-yl)malonate Diethyl 2-[6,7-dichloro-2-(3-chloro-2-butenyl)-2,3-dihydro-1-oxo-2-propyl-1H-inden-5-yl]malonate (10.7 g, 0.0218 mole) dissolved in toluene (45 ml) was added dropwise with stirring under N₂ at 25° C. to a suspension of 56% sodium hydride/mineral (1.22 g, 0.0284 mole) in dimethylformamide (45 ml). Methyl bromoacetate (4.34 g, 0.0284 mole) was added in one portion 40 minutes after the previous addition and the mixture was heated at 65° for 4½ hours. The mixture was then cooled, and after acetic acid (3 ml) was added, poured into ice water and extracted with diethyl ether. The organic extracts were washed with water, dried over MgSO₄, concentrated under vacuum, and the residue was chromatographed on silica eluting with methlene chloride/hexane, 4/1 to obtain 10.9 g of the product as an oil.

Step B: [6,7-Dichloro-2-(3-chloro-2-butenyl)-2,3-dihydro-1-oxo-2-propyl-1H-inden-5-yl]succinic acid Diethyl methoxycarbonylmethyl[6,7-dichloro-2-(3-chloro-2-butenyl)-2,3-dihydro-1-oxo-2-propyl-1H-inden-5-yl]malonate (10.7 g, 0.019 mole) was stirred at reflux for 2½ hours in a mixture of methanol (120 ml), water (120 ml) and sodium hydroxide (6 g). The solution was cooled, diluted with water, acidified with hydrochloric acid, and extracted with methylene chloride. The organic extracts were washed with water, dried over MgSO₄ and concentrated to obtain 8.0 g of the product as a gum.

Step C: 3-[6,7-Dichloro-2-(3-chloro-2-butenyl)-2,3-dihydro-1-oxo-2-propyl-1H-inden-5-yl]propionic acid
[6,7-Dichloro-2-(3-chloro-2-butenyl)-2,3-dihydro-1-oxo-2-propyl-1H-inden-5-yl]succinic acid (7.9 g, 0.01764 mole) was combined with quinoline (70 ml) and copper powder (2.9 g), stirred under N₂ at 130°-135° C. (internal) in an oil bath for ½ hour. The mixture was poured into ice water, acidified with hydrochloric acid and extracted with methylene chloride. The organic extracts were washed with dilute HCl, H₂O, dried over MgSO₄ and concentrated under vacuum. The residue was chromatographed on silica eluting with methylene chloride, tetrahydrofuran, acetic acid (100:1:1) to obtain 7 g of the product as an oil.

Step D:
3-[6,7-Dichloro-2,3-dihydro-1-oxo-2-(3-oxo-butyl)-2-propyl-1H-inden-5-yl]propionic acid 3-[6,7-Dichloro-2-(3-chloro-2-butenyl)-2,3-dihydro-1-oxo-2-propyl-1H-inden-5-yl]propionic acid (6.8 g, 0.0168 mole) dissolved in methylene chloride (65 ml) was added over 15 minutes to a mixture of sulfuric acid (75 ml) and methylene chloride (35 ml) at 5° C., stirred at 5° C. for 1 hour, poured over ice and water, and extracted with methylene chloride. The organic extracts were washed with water, dried over MgSO₄ and concentrated under vacuum. The residue was recrystallized from butyl chloride to obtain the product mp 131°-3° C.

| Calc for $C_{19}H_{22}Cl_2O_4$: | C, 59.23 | Found: | 59.47 |
|---|---|---|---|
| | H, 5.76 | | 5.90 |

Step E:
3-(5,6-Dichloro-2,3,9,9a-tetrahydro-3-oxo-9a-propyl-1H-fluoren-7-yl)propionic acid 3-[6,7-Dichloro-2,3-dihydro-1-oxo-2-(3-oxobutyl)-2-propyl-inden-5-yl]propionic acid (3.1 g, 0.00805 mole) was stirred at 25° C. in a mixture of methanol (2 ml), water (6 ml) and 1N sodium hydroxide (25 ml) for 96 hours. After dilution with water, the mixture was acidified with hydrochloric acid and extracted with a mixture of diethyl ether and tetrahydrofuran. The organic extracts were washed with water, dried over MgSO₄ and concentrated under vacuum. The residue was recrystallized from acetic acid-acetonitrile (1:1) to obtain the product mp 201°-3° C.

| Calc for $C_{19}H_{20}Cl_2O_3$: | C, 62.13 | Found: | 61.82 |
|---|---|---|---|
| | H, 5.49 | | 5.45 |

EXAMPLE 4

Resolution of (5,6-Dichloro-2,3,9,9a-tetrahydro-3-oxo-9a-propyl-1H-fluoren-7-yl)acetic acid Racemic (5,6-dichloro-2,3,9,9a-tetrahydro-3-oxo-9a-propyl-1H-fluoren-7-yl)acetic acid (32.9 g, 93 mMole) in acetonitrile (2.5 liters) is heated to boiling and cinchonidine (27.4 g, 93 mMole) is added. The solution is stirred at 5° C. for 24 hours and the solid that separated is filtered off, washed with acetonitrile and the filtrate is (I) saved. The salt is recrystallized from acetonitrile and the product removed by filtration, dried, treated with 1N hydrochloric acid (450 mL) and extracted with 20% tetrahydrofuran in diethyl ether. The extract is dried over MgSO₄; the solvent was evaporated in vacuo to give a pure enantiomer.

Filtrate (I) is evaporated in vacuo, treated with 2N HCl (400 mL), extracted with 20% tetrahydrofuran in diethyl ether and the extract was dried over MgSO₄. The solvent is evaporated in vacuo and the residue dissolved in acetonitrile (2.5 Liters), heated to boiling and cinchonidine (27.4 g, 93 mMole) is added. The solution is cooled to 5° C. and stirred for 24 hours. The solid that separates is worked up as described for the first enantiomer to give the second (opposite enantiomer).

EXAMPLE 5

Resolution of 3-(5,6-dichloro-2,3,9,9a-tetrahydro-3-oxo-9a-propyl-1H-fluoren-7-yl)propionic acid By carrying out the reaction as described in Example 4 except that the (5,6-dichloro-2,3,9,9a-tetrahydro-3-oxo-9a-propyl-1H-fluoren-7-yl)acetic acid is replaced by an equimolar quantity of 3-(5,6-dichloro-2,3,9,9a-tetrahydro-3-oxo-9a-propyl-1H-fluoren-7-yl)propionic acid there is obtained the two enantiomers of the title compound.

EXAMPLE 6

(5,6-Dichloro-2,3,9,9a-tetrahydro-3-oxo-9a-propyl-1H-fluoren-1-yl)ethanimidamide Step A:
[5,6-Dichloro-2,3,9,9a-tetrahydro-3-oxo-9a-propyl-1H-fluoren-7-yl)acetamide 5,6-Dichloro-2,3,9,9a-tetrahydro-3-oxo-9a-propyl-1H-fluoren-7-yl)acetic acid (7.34 g, 20 mMole) is dissolved in tetrahydrofuran (100 ml) and 1,1'-carbonyldiimidazole (3.2 g, 20 mMole) added and the mixture stirred at ambient temperature for 1 hour. Then ammonia gas is admitted below the surface of the stirring solution for one hour and the mixture stirred for 20 hours. The solvent is removed at reduced pressure and the residue treated with water. Extraction of the product with ether, followed by drying over MgSO₄ and evaporation of the solvent gives the desired amide.

Step B:
(5,6-Dichloro-2,3,9,9a-tetrahydro-3-oxo-9a-propyl-1H-fluoren-7-yl)acetonitrile (5,6-Dichloro-2,3,9,9a-tetrahydro-3-oxo-9a-propyl-1H-fluoren-7-yl)acetamide (7.03 g, 20 mMole) is dissolved in pyridine (50 ml) and 1,3-dicyclohexylcarbodiimide (4.35 g, 21.1 mMole) in pyridine (25 ml) is added with stirring at 15°-20° C. over a period of 30 minutes. The mixture is stirred at 20° C. for 3 hours and the precipitated dicyclohexylurea removed by filtration and the filtrate concentrated in vacuo to remove the pyridine. Addition of water gave the nitrile which is extracted with ether, dried over MgSO₄ and the solvent evaporated to give the pure nitrile.

Step C:
(5,6-Dichloro-2,3,9,9a-tetrahydro-3-oxo-9a-propyl-1H-fluoren-7-yl)ethanimidamide hydrochloride (5,6-Dichloro-2,3,9,9a-tetrahydro-3-oxo-9a-propyl-1H-fluoren-7-yl)-acetonitrile (3.34 g, 10 mMole) is dissolved in chloroform (40 ml) and ethanol (650 mg, 10.9 mMole) and the mixture cooled to 0° C. The mixture is stirred and saturated with hydrogen chloride gas. After standing for 16 hours, the mixture is basified by the dropwise addition of 10 normal sodium hydroxide. The resultant chloroform solution of the imino ester free base is washed with water, dried over K₂CO₃ and the chloroform removed by evaporation in vacuo. The residue consisting of the imino ether is dissolved in ethanol (30 ml) and water (5 ml) then ammonium chloride (700 ml, 13 mMole) is added and the mixture stirred at room temperature for 4 hours. The mixture is filtered to remove the excess ammonium chloride and the filtrate evaporated in vacuo. Treatment with acetone gave the product which was recrystallized from a mixture of ethanol and diethyl ether.

EXAMPLE 7

Parenteral solution of the Sodium Salt of (5,6-Dichloro-2,3,9,9a-tetrahydro-3-oxo-9a-propyl-1H-fluoren-7-yl)acetate The (5,6-dichloro-2,3,9,9a-tetrahydro-3-oxo-9a-propyl-1H-fluoren-7-yl)acetic acid (Example 2) (500 mg) is dissolved by stirring and warming with a solution of 0.25N sodium bicarbonate (5.6 ml). The solution is diluted to 10 ml with water and sterilized by filtration. All the water that is used in the preparation is pyrogen-free. The concentration of the active ingredient (calculated as free acid) in the final solution is 5%.

EXAMPLE 8

Parenteral solution of the (+) enantiomer of the sodium salt of (5,6-Dichloro-2,3,9,9a-tetrahydro-3-oxo-9a-propyl-1H-fluoren-7-yl)acetate The (+) (5,6-dichloro-2,3,9,9a-tetrahydro--oxo-9a-propyl-1H-fluoren-7-yl)acetic acid (Example 4) (500 mg) is dissolved by stirring and warming with a solution of 0.25N sodium bicarbonate (5.6 ml). The solution is diluted to 10 ml with water and sterilized by filtration. All the water that is used in the preparation is pyrogen-free. The concentration of the active ingredient (calculated as free acid) in the final solution is 5%.

Similar parenteral solutions can be prepared by replacing the active ingredient of this Example by any of the other compounds of this invention.

EXAMPLE 10

| Dry-Filled Capsules Containing 100 mg of Active Ingredient (free base) Per Capsule | |
|---|---|
| | Per Capsule |
| (5,6-Dichloro-2,3,9,9a-tetrahydro-3-oxo-9a-propyl-1H—fluoren-7-yl)-ethanimidamide hydrochloride | 100 mg |
| Lactose | 99 mg |
| Magnesium Stearate | 1 mg |
| Capsule (Size No. 1) | 200 mg |

The (5,6-dichloro-2,3,9,9a-tetrahydro-3-oxo-9a-propyl-1H-fluoren-7-yl)ethanimidamide hydrochloride (Example 6) is reduced to a No. 60 powder and then the lactose and magnesium stearate are passed through a No. 60 bolting cloth onto the powder and the combined ingredients admixed for 10 minutes and then filled into a No. 1 dry gelatin capsule.

Similar capsules can be prepared by replacing the active ingredient of this Example by any of the other compounds of this invention.

What is claimed is:

1. A compound of the formula:

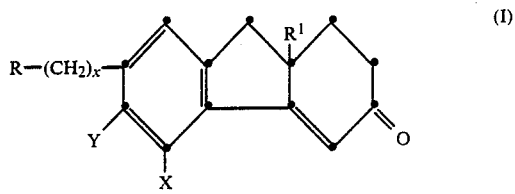

wherein:
R is —COOH;
R¹ is lower alkyl, branched or unbranched, containing from 1 to 5 carbon atoms, phenyl, p-fluorophenyl, o-fluorophenyl, p-chlorophenyl, benzyl, cycloalkyl containing from 3 to 6 nuclear carbon atoms, or cycloalkyl-lower alkyl containing from 4 to 7 total carbon atoms;
X and Y are halo or lower alkyl; and
x is 1 to 4.

2. A compound of the formula:

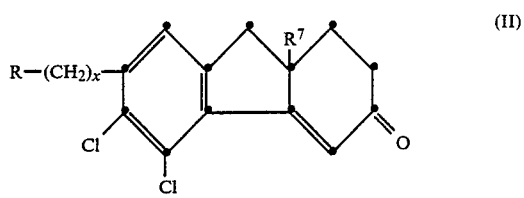

wherein:
R is —COOH;
R⁷ alkyl, branched or unbranched, containing from 1 to 5 carbon atoms; and
x is 1 or 2.

3. A compound according to claim 1, which is (5,6-dichloro-2,3,9,9a, tetrahydro-3-oxo-9a-propyl-1H-fluoren-7-yl)acetic acid.

4. A compound of claim 1, which is 3-(5,6-dichloro-2,3,9,9a-tetrahydro-3-oxo-9a-propyl-1H-fluoren-7-yl)propionic acid.

5. A compound of claim 4, which is the (+) enantiomer.

6. A compound of claim 6, which is the sodium salt.

7. A pharmaceutical composition useful in the treatment of brain injury comprising a pharmaceutical carrier and an effective amount of a compound of claim 1.

8. A pharmaceutical composition useful in the treatment of brain injury comprising a pharmaceutical carrier and an effective amount of a compound of claim 3.

9. A method of treating a person with brain injury which comprises administering to such a person an effective amount of a compound of claim 1.

10. A method according to claim 9, which comprises administering to a person with brain injury an effective amount of a compound of claim 3.

* * * * *